(12) United States Patent
Agar

(10) Patent No.: US 9,568,477 B2
(45) Date of Patent: Feb. 14, 2017

(54) SYSTEM AND METHOD FOR ANALYSIS OF BIO-METABOLITES FOR-USE IN IMAGE-GUIDED SURGERY

(71) Applicant: Nathalie Agar, Newton, MA (US)

(72) Inventor: Nathalie Agar, Newton, MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/655,854

(22) PCT Filed: Dec. 30, 2013

(86) PCT No.: PCT/US2013/078260
§ 371 (c)(1),
(2) Date: Jun. 26, 2015

(87) PCT Pub. No.: WO2014/106165
PCT Pub. Date: Jul. 3, 2014

(65) Prior Publication Data
US 2015/0338413 A1    Nov. 26, 2015

Related U.S. Application Data

(60) Provisional application No. 61/747,330, filed on Dec. 30, 2012, provisional application No. 61/894,595, filed on Oct. 23, 2013.

(51) Int. Cl.
*H01J 49/00*    (2006.01)
*G01N 33/574*   (2006.01)
(Continued)

(52) U.S. Cl.
CPC ......... *G01N 33/57484* (2013.01); *A61B 5/061* (2013.01); *A61B 10/02* (2013.01);
(Continued)

(58) Field of Classification Search
CPC .. G01N 33/57484; G01N 33/574; H01J 49/04; H01J 49/26; A61B 5/061; A61B 10/02; A61B 19/5244; G06F 19/18; G06F 19/24
(Continued)

(56) References Cited

U.S. PATENT DOCUMENTS 8,883,438 B2 * 11/2014 Cantley ............. A61K 31/4184
435/26
2007/0117164 A1 * 5/2007 Raskov ............ G01N 33/57419
435/7.23
(Continued)

FOREIGN PATENT DOCUMENTS

CA      2526878 A1   10/2004
WO    2011050211 A2    4/2011
WO  WO 2011050211 A2 *  4/2011  ......... A61K 31/4184

OTHER PUBLICATIONS

Agar, et al., Development of Stereotactic Mass Spectrometry for Brain Tumor Surgery, Neurosurgery, 2011, 68(2):280-290.
(Continued)

*Primary Examiner* — Michael Maskell
(74) *Attorney, Agent, or Firm* — Quarles & Brady LLP

(57) ABSTRACT

A system for identifying a bio-marker using mass spectroscopy is provided that includes a sample receptacle configured to receive a tissue sample, a mass spectrometry apparatus configured to receive the tissue sample and analyze the tissue sample using a mass spectrometry process to generate mass spectrometry data, and a computer system that includes a computer processor having access to a non-transitory, computer-readable storage medium having stored thereon instructions. The instructions cause the computer processor to: receive the mass spectrometry data from the mass spectrometry apparatus; analyze the mass spectrometry data to determine a presence of 2-Hydroxyglutarate (2-HG) in the tissue sample; and generate a report indicating
(Continued)

a health of the tissue sample based on the presence of 2-HG in the tissue sample.

18 Claims, 10 Drawing Sheets

(51) Int. Cl.
  *H01J 49/04* (2006.01)
  *A61B 5/06* (2006.01)
  *H01J 49/26* (2006.01)
  *G06F 19/18* (2011.01)
  *A61B 10/02* (2006.01)
  *G06F 19/24* (2011.01)

(52) U.S. Cl.
  CPC .......... *G01N 33/574* (2013.01); *G06F 19/18* (2013.01); *H01J 49/04* (2013.01); *H01J 49/26* (2013.01); *A61B 34/20* (2016.02); *G06F 19/24* (2013.01)

(58) Field of Classification Search
  USPC .................................. 250/281, 282; 436/173
  See application file for complete search history.

(56) References Cited

U.S. PATENT DOCUMENTS

| | | | |
|---|---|---|---|
| 2011/0144476 | A1 | 6/2011 | Jolesz et al. |
| 2012/0121554 | A1* | 5/2012 | Pappan .................. A61K 31/00 424/93.7 |
| 2013/0273560 | A1* | 10/2013 | Cooks .................... G01N 27/62 435/7.1 |
| 2013/0316385 | A1* | 11/2013 | Cantley .............. A61K 31/4184 435/26 |

OTHER PUBLICATIONS

Amary, et al., IDH1 and IDH2 Mutations are Frequent Events in Central Chondrosarcoma and Central and Periosteal Chondromas But Not in Other Mesenchymal Tumours, Journal of Pathology, 2011, 224(3):334-343 [Abstract Only].
Andronesi, et al., Detection of 2-Hydroxyglutarate in IDH-mutated Glioma Patients by Spectral-editing and 2D Correlation Magnetic Resonance Spectroscopy, Science Translational Medicine, 2012, 4(116):116ra4.
Blackie, et al., Histological Appearances of Intracranial Biopsies Obtained Using the Cavitron Ultrasonic Surgical Aspirator, J. Clin. Pathol., 1984, 37:1101-1104.
Borger, et al., Frequent Mutation of Isocitrate Dehydrogenase (IDH)1 and IDH2 in Cholangiocarcinoma Identified Through Broad-Based Tumor Genotyping, The Oncologist, 2012, 17:72-79.
Capper, et al., Characterization of R132H Mutation-Specific IDH1 Antibody Binding in Brain Tumors, Brain Pathology, 2010, 20(1):245-254.
Choi, et al., 2-Hydroxyglutarate Detection by Magnetic Resonance Spectroscopy in IDH-Mutated Glioma Patients, Nature Medicine, 2012, 18(4):624-629.
Dang, et al., Cancer-Associated IDH1 Mutations Produce 2-Hydroxyglutarate, Nature, 2009, 462(7274):739-744.
Dias-Santagata, et al., Rapid Targeted Mutational Analysis of Human Tumours: A Clinical Platform to Guide Personalized Cancer Medicine, EMBO Molecular Medicine, 2010, 2:146-158.
Dill, et al. Lipid Profiles of Canine Invasive Transitional Cell Carcinoma of the Urinary Bladder and Adjacent Normal Tissue by Desorption Electrospray Ionization Imaging Mass Spectrometry, Anal. Chem., 2009, 81(21):8758-8764.
Dorward, et al., The Advantages of Frameless Stereotactic Biopsy Over Frame-Based Biopsy, British Journal of Neurosurgery, 2002, 16(2):110-118 [Abstract Only].

Eberlin, et al., Discrimination of Human Astrocytoma Subtypes by Lipid Analysis Using Desorption Electrospray Ionization Imaging Mass Spectrometry, Angew. Chem. Int. Ed. Engl., 2010, 49(34):5953-5956.
Eberlin, et al., Classifying Human Brain Tumors by Lipid Imaging with Mass Spectrometry, Cancer Research, 2011, 72(3):645-654.
Elhawary, et al., Intra-Operative Real-Time Querying of White Matter Tracts During Frameless Stereotactic Neuronavigation, Neurosurgery, 2011, 68(2):506-516.
Elkhaled, et al., Magnetic Resonance of 2-Hydroxyglutarate in IDH1-Mutated Low-Grade Gliomas, Science Translational Medicine, 2012, 11:4(116):116ra5.
Guo, et al., The Relationship Between Cho/NAA and Glioma Metabolism: Implementation for Margin Delineation of Cerebral Gliomas, Acta Neurochirurgica, 2012, 154(8):1361-1370.
Jolesz, et al., Intraoperative Imaging in Neurosurgery: Where Will the Future Take Us?, Acta Neurochir. Suppl., 2011, 109:21-25.
Kalinina, et al., Detection of "Oncometabolite" 2-Hydroxyglutarate by Magnetic Resonance Analysis as a Biomarker of IDH1/2 Mutations in Glioma, J. Mol. Med. (Berl), 2012, 90(10):1161-1171.
Kelly, Stereotactic Surgery: What Is Past Is Prologue, Neurosurgery, 2000, 46(1):16-27.
Koivunen, et al., Transformation by the R Enantiomer of 2-Hydroxyglutarate Linked to EgIN Activation, Nature, 2012, 483(7390):484-488.
Krieger, et al., Role of Stereotactic Biopsy in the Diagnosis and Management of Brain Tumors, Seminars in Surgical Oncology, 1998, 14:13-25.
Linehan, et al., The Genetic Basis of Kidney Cancer: A Metabolic Disease, Nat. Rev. Urol., 2010, 7(5):277-285.
Lu, et al., IDH Mutation Impairs Histone Demethylation and Results in a Block to Cell Differentiation, Nature, 2012, 483(7390):474-478.
Malhotra, et al., Evaluation of Histological Appearance of Tissues Removed by Cavitron Ultrasonic Surgical Aspirator (CUSA), Acta Neurochir. (Wien), 1986, 81:132-134.
Mardis, et al., Recurring Mutations Found by Sequencing an Acute Myeloid Leukemia Genome, N. Engl. J. Med., 2009, 361(11):1058-1066.
Parsons, et al., An Integrated Genomic Analysis of Human Glioblastoma Multiforme, Science, 2008, 321(5897):1807.
Pope, et al., Non-Invasive Detection of 2-Hydroxyglutarate and Other Metabolites in IDH1 Mutant Glioma Patients Using Magnetic Resonance Spectroscopy, J. Neurooncol., 2012, 107(1):197-205.
Poza, et al., Intracranial Tumor Biopsy—CT-Guided Stereotactic Surgery, Appl. Neurophysiol., 1985, 48(1-6):482-487 [Abstract Only].
Richmond, et al., Evaluation of the Histopathology of Brain Tumor Tissue Obtained by Ultrasonic Aspiration, Neurosurgery, 1983, 13(4):415-419.
Takats, et al., Mass Spectrometry Sampling Under Ambient Conditions with Desorption Electrospray Ionization, Science, 2004, 306:471-473.
Turcan, et al., IDH1 Mutation is Sufficient to Establish the Glioma Hypermethylator Phenotype, Nature, 2012, 483(7390):479-483.
Weller, et al., Isocitrate Dehydrogenase Mutations: A Challenge to Traditional Views on the Genesis and Malignant Progression of Gliomas, Glia, 2011, 59(8):1200-1204 [Abstract Only].
Wiseman, et al., Ambient Molecular Imaging by Desorption Electrospray Ionization Mass Spectrometry, Nature Protocols, 2008, 3(3):517-524.
Wiseman, et al., Desorption Electrospray Ionization Mass Spectrometry: Imaging Drugs and Metabolites in Tissues, PNAS, 2008, 105(47):18120-18125.
Xu, et al., Oncometabolite 2-Hydroxyglutarate Is a Competitive Inhibitor of a-Ketoglutarate-Dependent Dioxygenases, Cancer Cell, 2011, 19:17-30.
Ye, et al., From Pixel to Voxel: A Deeper View of Biological Tissue by 3D Mass Spectral Imaging, Bioanalysis, 2011, 3(3):313-332.
PCT International Search Report and Written Opinion, PCT/US2013/078260, Apr. 10, 2014.

* cited by examiner

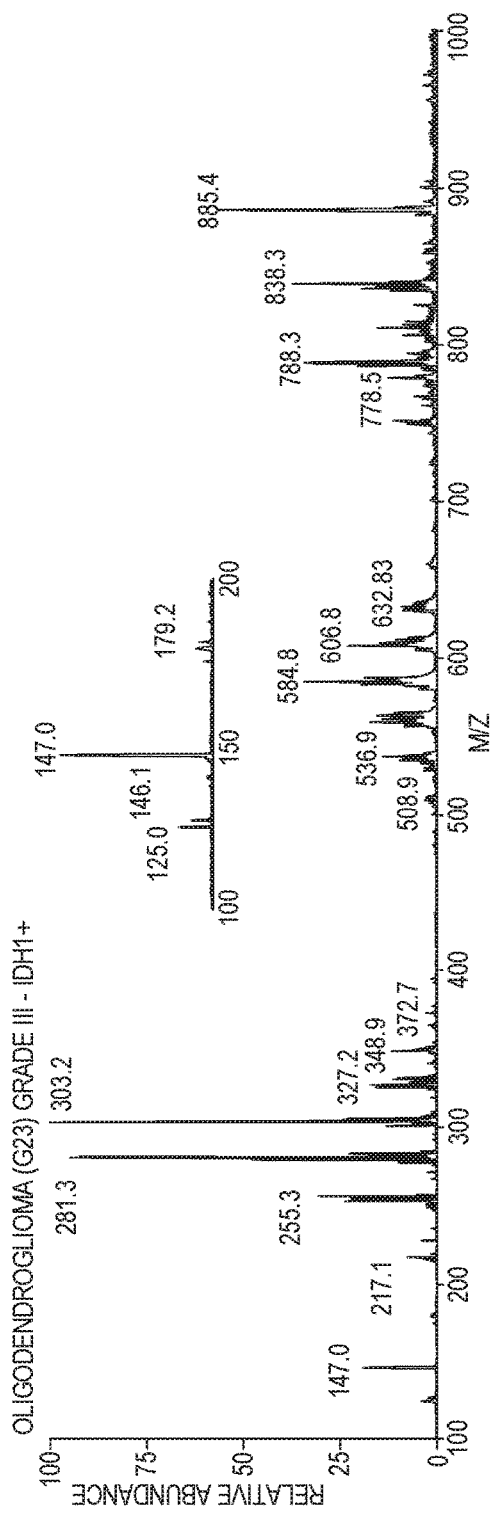
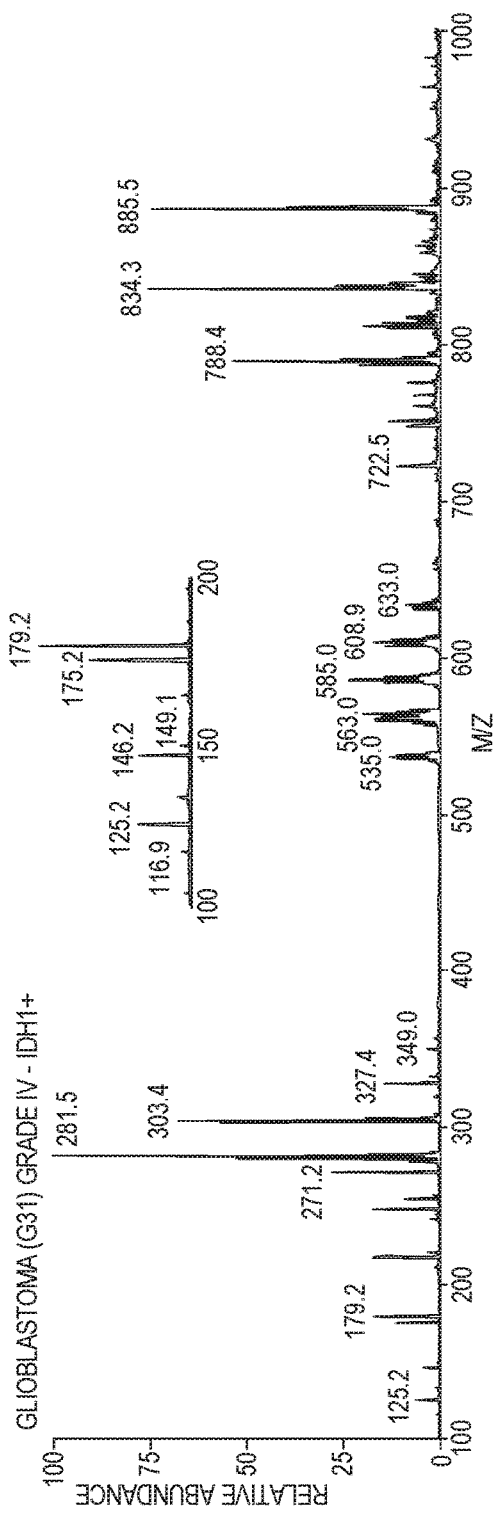
FIG. 2a
FIG. 2b

| Glioma Samples | | | | | MeOH:H2O | | | DMF:ACN | | |
|---|---|---|---|---|---|---|---|---|---|---|
| Code | Diagnosis | IDH status IHC | DESI - 2HG | % tumor | m/z 147 | Sum lipids | (147/SUM)*1000 | m/z 147 | Sum lipids | (147/SUM)*1000 |
| POSITIVE SAMPLES | | | | | | | | | | |
| G2 | Astrocytoma | positive | positive | 60 | 21 | 2174 | 10 | 50 | 680 | 74 |
| G21 | Oligoastrocytoma | positive | positive | 95 | 317 | 10105 | 31 | 211 | 853 | 247 |
| G23 | Oligodendroglioma | positive | positive | 95 | 214 | 4776 | 45 | 204 | 950 | 215 |
| G30 | Glioblastoma | positive | positive | 80 | 152 | 2893 | 53 | 86 | 1776 | 48 |
| G41 | Oligodendroglioma | positive | positive | 95 | 64 | 3657 | 18 | 131 | 738 | 178 |
| | oct | positive | positive | 95 | 93 | 2916 | 32 | 196 | 860 | 228 |
| G42 | Oligodendroglioma | positive | positive | dense | 51 | 4181 | 12 | 123 | 829 | 148 |
| | oct | positive | positive | dense | 75 | 2060 | 36 | 313 | 1300 | 241 |
| G43 | Oligodendroglioma | positive | positive | 80% | 393 | 8386 | 47 | 37 | 758 | 49 |
| G45 | Oligoastrocytoma | positive | positive | 100% | 119 | 5119 | 23 | 98 | 1236 | 79 |
| G49 | Oligodendroglioma | positive | positive | 100% | 40 | 1540 | 26 | 121 | 1385 | 87 |
| G33 | Glioblastoma | negative | positive | 80% | 55 | 6003 | 9 | 48 | 1179 | 41 |
| G28 | Glioblastoma | negative | positive | 80% | 107 | 5375 | 20 | 137 | 1086 | 126 |
| G46 | Glioblastoma | positive | positive | 90% | 60 | 1936 | 31 | 73 | 1174 | 62 |
| | oct | positive | positive | 95% | 176 | 3961 | 44 | 106 | 1454 | 73 |
| Average Positive with HIGH tumor cell % | | | | | 129 | | 29 | 129 | | 126 |
| G9 | Oligodendroglioma | positive | positive | 50 | 12 | 6914 | 2 | 68 | 1543 | 44 |
| G10 | Oligodendroglioma | positive | positive | 30 | 6 | 7083 | 1 | 23 | 1936 | 12 |
| G13 | Oligoastrocytoma | positive | positive | 5 | 4 | 770 | 5 | 15 | 1412 | 11 |
| G14 | Oligoastrocytoma | positive | positive | 40 | 18 | 926 | 19 | 52 | 1112 | 47 |
| G20 | Oligoastrocytoma | positive | positive | 30 | 63 | 32120 | 2 | 42 | 2686 | 16 |
| G22 | Oligodendroglioma | positive | positive | 10 | 25 | 98401 | 0 | 34 | 3861 | 9 |
| G25 | Oligodendroglioma | positive | positive | 20 | 53 | 2625 | 20 | 82 | 1145 | 72 |
| G26 | Glioblastoma | scattered cells | positive | 20 | 52 | 10350 | 5 | 40 | 768 | 52 |
| G11 | Oligodendroglioma | | positive | 20 | 16 | 1543 | 10 | 48 | 604 | 79 |
| G47 | Glioblastoma | positive | positive | low | 27 | 2808 | 10 | 22 | 744 | 30 |
| | oct | positive | positive | low | 34 | 38082 | 1 | 37 | 2599 | 14 |
| G40 | Oligodendroglioma | positive | positive | low | | not available | | 54 | 1197 | 45 |
| Average Positive with LOW tumor cell % | | | | | 28 | | 7 | 43 | | 36 |

FIG. 11a

| | NEGATIVE SAMPLES | | | | | | | |
|---|---|---|---|---|---|---|---|---|
| G3 | Astrocytoma | negative | 60 | 4 | 653 | 6 | 16 | 1575 | 10 |
| G5 | Glioblastoma | negative | 80 | 5 | 1308 | 4 | 20 | 698 | 29 |
| G6 | Glioblastoma | negative | 80 | 5 | 1157 | 4 | 15 | 1219 | 12 |
| G8 | Glioblastoma | negative | 90 | 5 | 1183 | 4 | 12 | 1182 | 10 |
| G31 | Glioblastoma | negative | 90 | 19 | 1538 | 12 | 28 | 1688 | 17 |
| G32 | Glioblastoma | negative | 90 | 16 | 2872 | 6 | 30 | 2037 | 15 |
| G35 | Glioblastoma | negative | 80 | 26 | 10149 | 3 | 19 | 523 | 36 |
| G27 | Glioblastoma | negative | 95 | 30 | 1944 | 15 | 15 | 934 | 16 |
| G48 | Glioblastoma | negative | | 10 | 5405 | 2 | 11 | 515 | 21 |
| G29 | Glioblastoma | negative | 80 | 14 | 84202 | 0 | 21 | 853 | 25 |
| G4 | Astrocytoma | negative | 30 | 17 | 3004 | 6 | 9 | 1412 | 6 |
| G34 | Glioblastoma | negative | 30 | 18 | 2406 | 7 | 14 | 1653 | 8 |
| | Average Negative with LOW tumor cell % | | | 14 | | 6 | 18 | | 17 |

FIG. 11b

| Surgical CASE 3 - IDH1 positive | | MeOH:H2O | | | | | |
|---|---|---|---|---|---|---|---|
| Code | Diagnosis | % tumor | m/z 147 | Sum lipids | (147/SUM)*1000 | m/z 788 | (147/788)*1000 |
| S17 | Oligodendroglioma | N.A. | 111 | 3370 | 33 | 202 | 550 |
| S18 | Oligodendroglioma | very dense | 421 | 12192 | 35 | 986 | 427 |
| S19 | Oligodendroglioma | very dense | 223 | 7165 | 31 | 339 | 658 |
| S20 | Oligodendroglioma | fairly dense | 147 | 10158 | 14 | 548 | 268 |
| S21 | Oligodendroglioma | not very dense | 106 | 6651 | 16 | 421 | 252 |
| S22 | Oligodendroglioma | very dense | 97 | 3034 | 32 | 211 | 460 |

FIG. 12

SYSTEM AND METHOD FOR ANALYSIS OF BIO-METABOLITES FOR-USE IN IMAGE-GUIDED SURGERY

CROSS-REFERENCE TO RELATED APPLICATIONS

This application represents the national stage entry of PCT International Application No. PCT/US2013/078260filed Dec. 30, 2013, which claims the benefit of U.S. Provisional Patent Application No. 61/747,330 filed Dec. 30, 2012 and U.S. Provisional Patent Application No. 61/894,595 filed on Oct. 23, 2013 the entire disclosures of which are hereby incorporated herein by reference for all purposes.

RELATED APPLICATIONS

This invention was made with government support under 5DP2OD007383-05 awarded by the National Institutes of Health. The government has certain rights in the invention.

BACKGROUND

The invention relates generally to intraoperative analysis of tissue using mass spectrometry.

The review of tissue sections by light microscopy remains a cornerstone of tumor diagnostics. In recent decades, monitoring expression of individual proteins using immunohistochemistry and characterizing chromosomal aberrations, point mutations, and gene expression with genetic tools has further enhanced diagnostic capabilities. These ancillary tests, however, often require days to perform and results become available long after surgery is completed. For this reason, the microscopic review of tissue biopsies frequently remains the sole source of intraoperative diagnostic information, with many important surgical decisions based on this information. This approach is time consuming, often requiring nearly 30 minutes or more between the moment a tissue is biopsied and the time the pathologist's interpretation is communicated back to the surgeon. Tools that provide immediate feedback to the surgeon could transform the way surgery is performed.

BRIEF SUMMARY OF THE INVENTION

The present invention overcomes the aforementioned drawbacks by providing mass spectrometry systems and methods that enable analysis of proteins and lipids of tissue tissues. For example, the ionization profile of lipids within tumors can be used for tumor classification and to provide valuable prognostic information such as tumor grade. As a further example, a system is provided that uses desorption electrospray ionization-mass spectrometry (DESI-MS) in ambient conditions with minimal pretreatment of the samples to perform analysis and, therefore, provide diagnostic information rapidly within various environments, including the operating room.

In accordance with one aspect of the invention, a system for identifying a bio-marker using mass spectroscopy is provided that includes a sample receptacle configured to receive a tissue sample, a mass spectrometry apparatus configured to receive the tissue sample and analyze the tissue sample using a mass spectrometry process to generate mass spectrometry data, and a computer system that includes a computer processor having access to a non-transitory, computer-readable storage medium having stored thereon instructions. The instructions cause the computer processor to: receive the mass spectrometry data from the mass spectrometry apparatus; analyze the mass spectrometry data to determine a presence of 2-Hydroxyglutarate (2-HG) in the tissue sample; and generate a report indicating a health of the tissue sample based on the presence of 2-HG in the tissue sample.

In accordance with another aspect of the invention, a method of identifying cancerous cells is provided and includes collecting a tissue sample, analyzing the tissue sample with a mass spectrometry system, determining a relative abundance of a mass-to-charge-ratio of about 147 m/z, and based at least in part on the determined relative abundance of 147 m/z, generating a report indicating a likelihood that the tissue sample includes cancerous cells.

In accordance with yet another aspect of the invention, a system for use in an operating room is provided and includes a sampling probe configured to collect a tissue sample, a mass spectrometry apparatus in communication with the sampling probe and configured to receive the tissue sample and analyze the tissue sample using a mass spectrometry process to generate mass spectrometry data, a computer system including a computer processor having access to a non-transitory, computer-readable storage medium having stored thereon instructions that cause the computer processor to: receive the mass spectrometry data from the mass spectrometry apparatus; analyze the mass spectrometry data to determine a relative abundance of 147 m/z indicating a presence of 2-Hydroxyglutarate (2-HG) in the tissue sample; access a database of at least one of bio-marker information and bio-marker analysis algorithms; and analyze the relative abundance of 147 m/z using the at least one of the bio-marker information and bio-marker analysis algorithms to determine a presence of 2-HG in the tissue sample. The system also includes a report generator configured to deliver a report indicating the likelihood of cancer in the tissue sample.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

FIG. 2a shows a negative ion mode DESI-MS mass spectra obtained in a linear ion trap mass spectrometer from m/z 100 to 1000 for sample G23, an oligodendroglioma with the IDH1 R132H mutant. Insets show zoom in region m/z 100-200.

FIG. 2b shows a negative ion mode DESI-MS mass spectra obtained in a linear ion trap mass spectrometer from m/z 100 to 1000 for sample G31, a glioblastoma with wild-type IDH1. Insets show zoom in region m/z 100-200.

FIG. 11a is a portion of detailed description of samples used in an IDH1 study. IHC and DESI results are shown, for both solvent systems used.

FIG. 11b is a portion of a detailed description of samples used in an IDH1 study. IHC and DESI results are shown, for both solvent systems used.

FIG. 12 shows 2-HG levels results for samples visualized in FIG. 10.

Figure 1A:
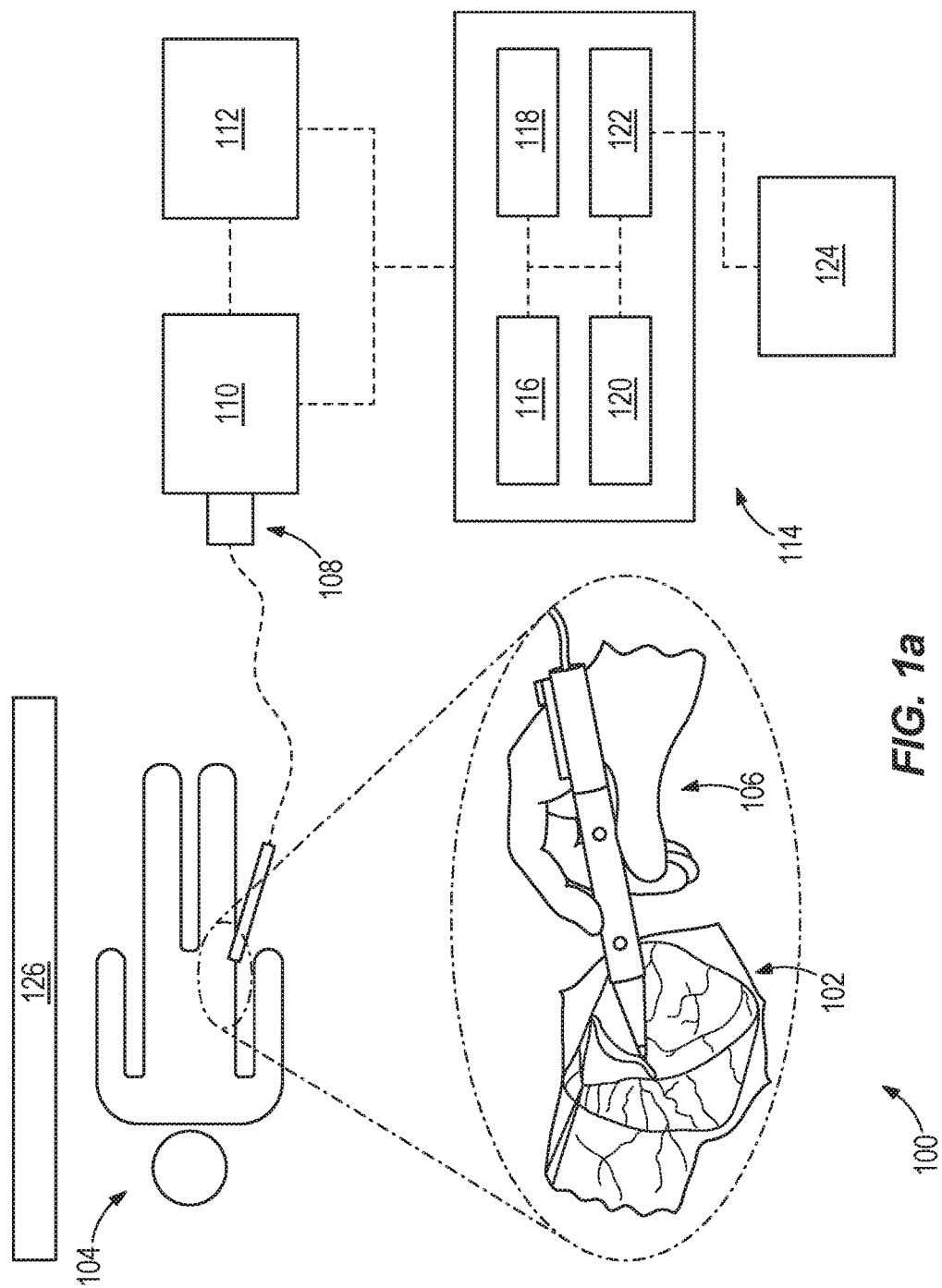
FIG. 1a is a schematic representation of a system for analyzing a tissue sample in accordance with the present invention.

Specific embodiments of the invention have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Mass spectrometry imaging (MSI) has been applied to investigate the molecular distribution of proteins, lipids, and metabolites without the use of labels. In particular, desorption electrospray ionization (DESI) allows direct tissue analysis with little or no sample preparation. Therefore, with the advantage of easy implementation, DESI mass spectrometry imaging (DESI-MSI) has great potential in the application of intra-operative tissue analysis. The present invention leverages spectroscopy in a manner that may include spatially encoded information correlated with the surgical site and/or the tissue histology itself. However, not all spectroscopy data in accordance with the present invention needs to be spatially encoded. For example, one or a series of points maybe sampled with or without spatial encoding information and delivered to the clinician. Furthermore, when the spectroscopy data is spatially encoded, the spatial encoding may include two or three-dimensional spatial encoding. Thus, the data may be presented in pixels or voxels.

Recurrent mutations have been described in the genes encoding isocitrate dehydrogenases 1 and 2 (IDH1 and IDH2) in a number of tumor types including gliomas, intrahepatic cholangiocarcinomas, acute myelogenous leukaemias (AML) and chondrosarcomas. These mutant enzymes have the unusual property of converting α-ketoglutarate to 2-hydroxyglutarate (2-HG). This oncometabolite has pleiotropic effects impacting DNA methylation patterns, and the activity of prolyl hydroxylase activity. While 2-HG is present in vanishingly small amounts in normal tissues, concentrations of several micromoles per gram of tumor have been found in tumors with mutations in IDH1 and IDH2.

The present invention provides for the detection of 2-hydroxyglutarate using 2-dimensional DESI-MS on a series of gliomas. Detecting metabolites in tumor tissues with precise spatial distribution and under ambient conditions provides a new paradigm for intraoperative surgical decision-making Thus, as will be described, the present invention provides systems and methods for, among other things, the detection of 2-hydroxyglutarate using 2-dimensional DESI-MS. The invention may apply to tumor boundary detection or to the recognition of other bio-markers for intra-operative analysis.

Turning to FIG. 1, an exemplary system 100 is provided that is designed to analyze a sample 102 acquired from a subject 104, particularly during an operative procedure, such as may be performed in an operating room. The system 100 may be configured for use with a tool or probe 106 to assist or work in conjunction with other systems for providing the sample 102 to a sample receptacle 108 of the system 100. For example, it is contemplated that the system may be compatible with systems or method or include systems disclosed in co-pending U.S. patent application Ser. No. 13/059,524, which is incorporated herein by reference in its entirety.

Once a sample is provided to the sample receptacle 108, the sample is processed by a mass-spectrometry system 110. The mass-spectrometry system 110 analyzes the tissue to determine a presence of a bio-marker. The mass-spectrometry system 110 may be a desorption electrospray ionization apparatus. In any case, the mass-spectrometry system 110 is coupled to a report generator 112 that is configured to deliver an analysis report that may indicate a likelihood of cancer remaining in the subject based on the analysis and, more particularly, any of a variety of bio-markers, such as will be further described. The analysis may provide other information or alternate information, as desired. For example, the analysis report may provide the levels of all target bio-markers. The report generator 112 may include a printing system to print a physical report, an audible feedback or other user interface, and/or may include a display to display a report, including figures and user-interface components, for example, such as will be described with respect to FIGS. 2-8 or those derived therefrom.

The mass-spectrometry system 110 and/or report generator 112 may include or be connected to a computer system 114. The computer system 114 includes a computer processor connected to a non-transitory, computer-readable storage medium or memory 118 that can store computer programs to control operation of the computer system 114 and, thereby, control operation of or coordinate operation with the mass-spectrometry system 110 and/or report generator 112. Accordingly, the computer system 114 may include any of a variety of user interfaces 120 or communications mechanisms, including a keyboard, mouse, touch screen, monitor, audio or video input or output, and the like. In addition, the computer system 114 may include an of a variety of input or communications connection 122, including traditional computer-system input/outputs, network communications ports (wired and wireless) that may provide access to wide and local networks and the Internet. By way of the communications connection 122, the computer system 114 may be coupled to a database 124 or other information repository. As will be described, the database 124 may store a variety of information to facilitate data analysis, including data on various bio-markers, such as will be described, and various algorithms or processes that the processor 116 may utilize the analyze information about the sample provided to the receptacle 108 and provide a report through the report generator 112.

Thus, in operation, the system 100 can be utilized within an operating room to provide real-time feedback to a surgeon or other clinician. In addition to the mass spectrometry results and the feedback regarding any of a variety of bio-markers and/or analysis algorithms, the probe 106 may also be coupled with additional navigation or recording systems, such as disclosed in co-pending U.S. patent application Ser. No. 13/059,524.

That is, the probe 106 may include stereotactic tracking elements or beacons that are linked to imaging components. In one construction, an imaging device 126 such as a magnetic resonance imaging (MRI), computed tomography (CT), positron emission tomography (PET), magnetic resonance spectroscopy (MRS), optical, or other imaging device is used to create a three-dimensional (3D) anatomical image of the surgery site. The stereotactic tracking elements may then be used to track the probe 106 within the anatomical image. In this way, the surgeon may track the location within an additional image of where the tissue sample was collected and correlate the report details, such as the spectroscopy images, to the exact location. In this way, the surgeon may use the 3D image as a map and examine various areas of the surgery site for the presence of bio-markers, for example through a report generator 112. Regardless of whether additional imaging or tracking systems are used, the system 100 provides the surgeon with real-time time and direct feedback about the operating site. This provides a very powerful tool for real-time feedback during medical procedures. For example, in the case of a cancer resection, the system 100 allows the surgeon or clinician completely remove the cancerous cells, while maintaining the maximum amount of healthy tissue in tact, because, as will be described, the feedback from the system 100 can indicate the presence or absence of cancer cells in real-time.

The report generator 112 is located within the operating room such that the surgeon can monitor the anatomical image, the probe location, and the spectroscopy data and image for any sampled point within the surgery site in real time. This provides the surgeon with more information about the surgery while he or she can still affect the outcome of the surgery without having to wait for lengthy lab procedures. The report generator 112 may include a visual monitor that includes a color display large enough to be easily read in an operating room environment. The display may be large enough such that it is easily read to reduce error of interpretation during surgery. The display can provide the anatomical image, the spectroscopy data and images, the stereotactic tracking information, and other information related to the surgery as desired.

Figure 1B:
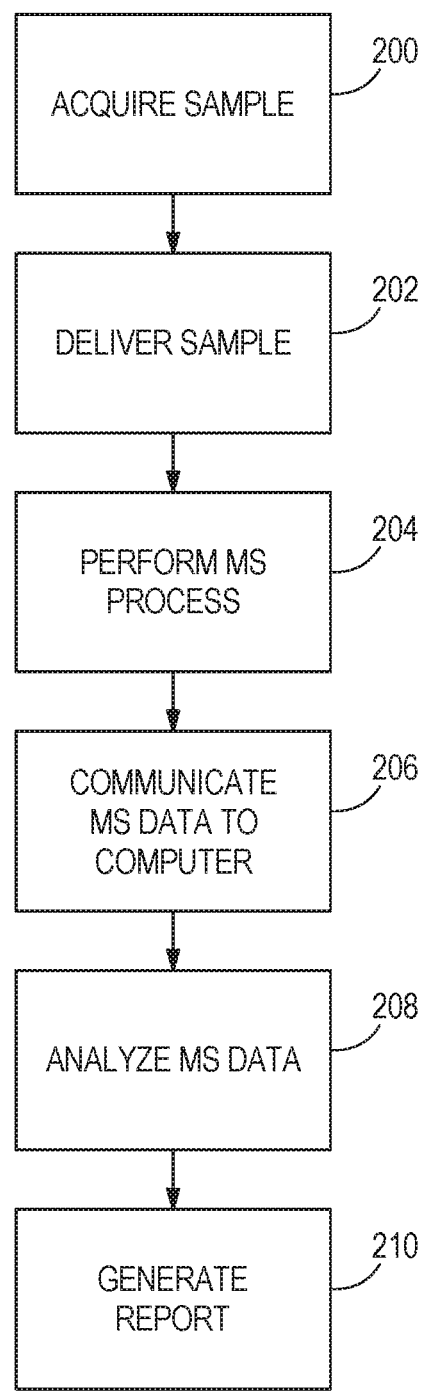
FIG. 1b is a flow chart setting forth a series of steps for analyzing a tissue sample in accordance with the present invention.

Referring to FIGS. 1A and 1B, a method for using a system such as described above with respect to FIG. 1A begins at process block 200 by acquiring a sample from the subject. The sample is acquired with a probe 106, such that the sample may be acquired from an intra-operative site and delivered at process block 202 to the receptacle 108 that is located within the operating room, for example, with minimal or no pathological processing. At process block 204, the receptacle 108 communicates with the mass-spectrometry system 110 to perform a mass-spectrometry process, which may be a DESI-MS process, on the sample. At process block 206, the results of the mass-spectrometry process are communicated to the computer system 114. That is, raw or pre-processed mass-spectrometry data, which may be spatially encoded, is provided to the computer system 114. At process block 208, the computer system 114 analyzes the mass-spectrometry data received from the mass-spectrometry system 110 to determine whether one or more bio-markers are present. For example, the computer system 114 may access the database 124 or other information systems to access information about one or more bio-markers and compare the mass-spectrometry data to the information about the one or more bio-markers to determine if a bio-marker is present in the mass-spectrometry data. At process block 210, the computer system 114 generates and communicates a report, including any information about the one or more bio-markers, in coordination with the report generator 112. This process can be performed in real-time by a clinician within the constraints of the operating room or other clinical setting. Thus, the present invention enables intra-operative analysis and feedback without the traditional delay presented by pathological analysis of intra-operatively acquired tissue samples.

Below, one specific bio-marker and its relation to analyzying tissue will be discussed. In particular, the present can leverage the discovery that 2-hydroxyglutarate (2-HG) can be detected in glioma tissues using two-dimensional DESI-MS. By monitoring 2-HG levels in tumor samples, at the time of surgery, this approach can provide rapid diagnostic information and actionable feedback.

Here, using gliomas with IDH1 mutations as an example, we show that a single metabolite analyzed in the operating room can rapidly provide highly relevant information such as tumor classification (e.g., 2-HG expressing central nervous system (CNS) tumors are nearly always gliomas), genotype information (e.g., 2-HG expressing tumors carry mutations in IDH1 or IDH2), prognostic information (e.g., 2-HG expressing tumors have a more favorable outcome) as well as intraoperative guidance for discriminating between tumor cells and normal brain tissue. The approach described herein may be applicable for the resection of all 2-HG producing tumors including chondrosarcoma and cholangiocarcinoma. 70-80 percent of grade II and grade III gliomas as well as the majority of secondary glioblastomas contain IDH mutations, therefore monitoring 2-HG with DESI-MS may be useful for many neurosurgical interventions.

Other metabolites such as succinate and fumarate, which accumulate in specific tumor types, may similarly prove to be valuable markers using DESI-MS approaches. As metabolomic discovery efforts intensify, the cadre of useful metabolite markers and signatures is expected to expand significantly. This will undoubtedly increase the breadth and potential of MS diagnostics.

During DESI-MS analysis in the negative ion mode, in its deprotonated form, 2-HG should be detected at an m/z of approximately 147. Together with the rich diagnostic lipid information commonly observed from gliomas by DESI-MS in the mass range m/z 200-1000, there exists an intense peak at m/z 147.2 in an IDH1 mutated sample (FIG. 2a), but not in an IDH1 wild-type sample (FIG. 2b). A much less intense peak (i.e., at approximately noise levels) was observed at m/z 147.1 for the IDH1 wild-type sample.

Figure 3:
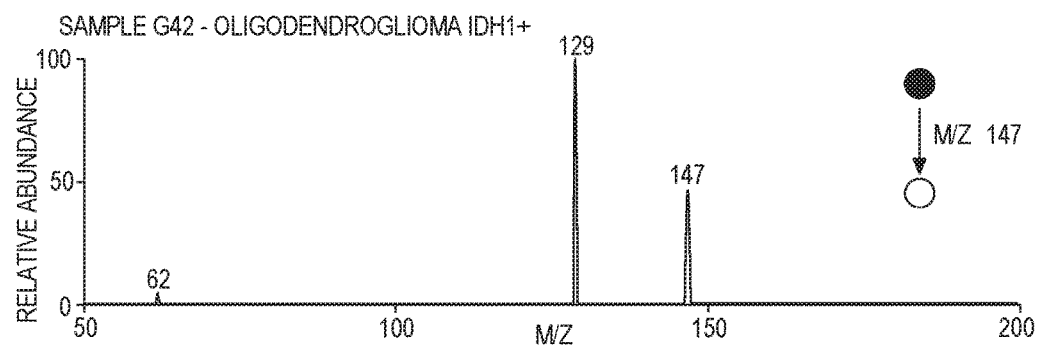
FIG. 3 shows a negative ion mode DESI-MS mass spectra obtained in a linear ion trap mass spectrometer from m/z 100 to 1000 for tandem mass spectra of m/z 147 detected from sample G42, an oligodendroglioma with the IDH1 R132H mutant $MS^2$.
Figure 4:
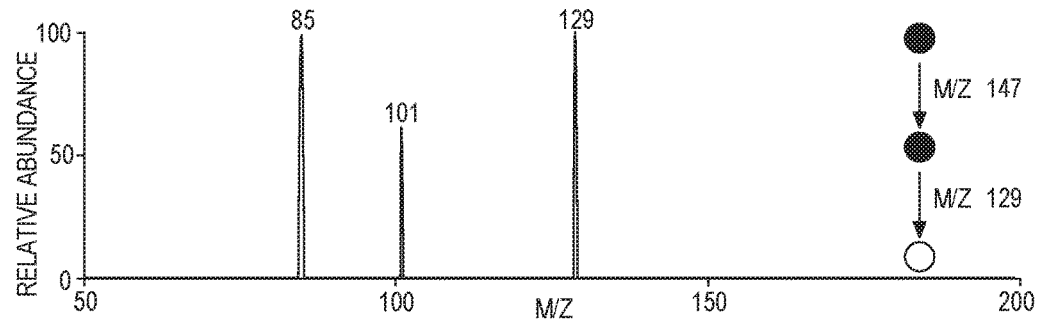
FIG. 4 shows a negative ion mode DESI-MS mass spectra obtained in a linear ion trap mass spectrometer from m/z 100 to 1000 for tandem mass spectra of m/z 147 detected from sample G42, an oligodendroglioma with the IDH1 R132H mutant $MS^3$.
Figure 5:
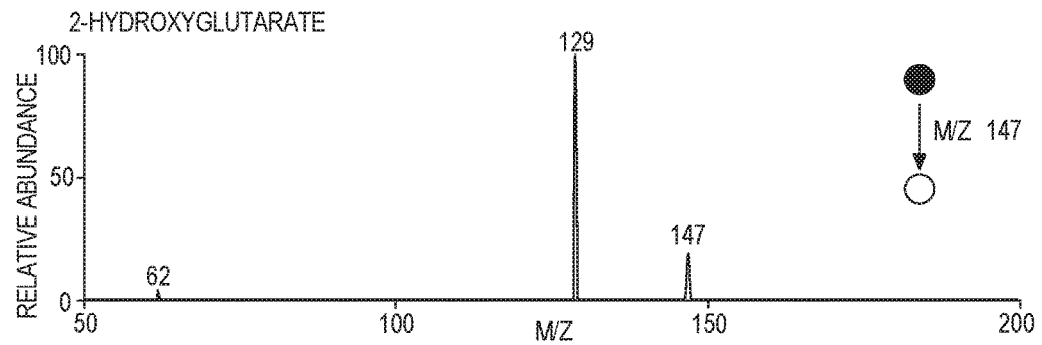
FIG. 5 shows a negative ion mode DESI-MS mass spectra obtained in a linear ion trap mass spectrometer from m/s 100 to 1000 for tandem mass spectra of m/z 147 detected from purified L-α-hydroxyglutaric acid $MS^2$.
Figure 6:
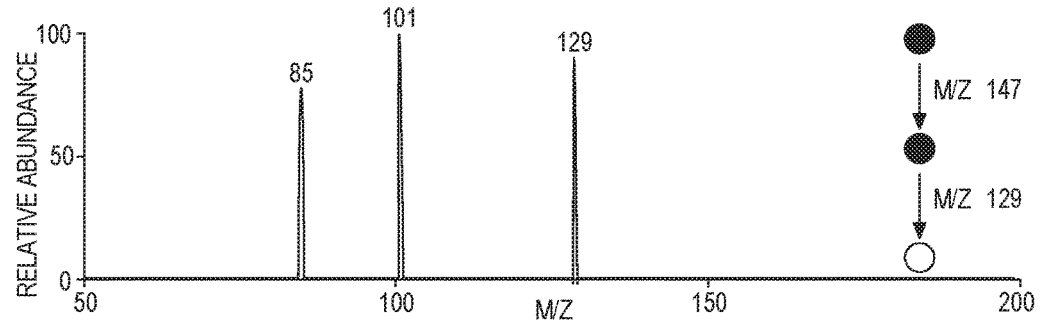
FIG. 6 shows a negative ion mode DESI-MS mass spectra obtained in a linear ion trap mass spectrometer from M/S 100 to 1000 for tandem mass spectra of m/z 147 detected from purified L-α-hydroxyglutaric acid $MS^3$.
Figure 7:
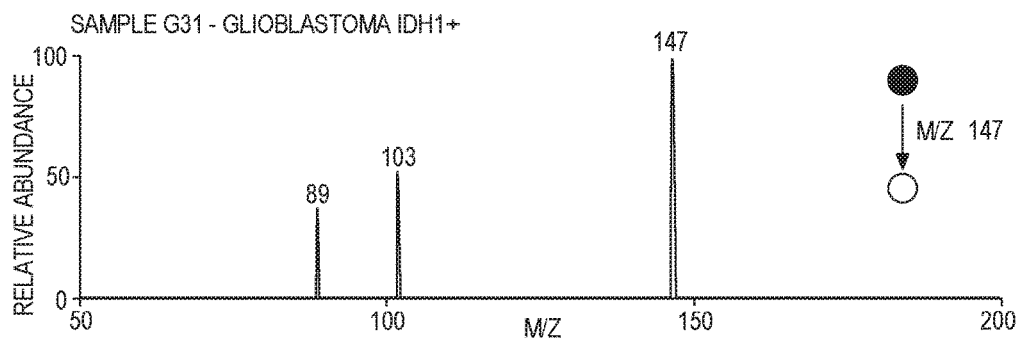
FIG. 7 shows a tandem mass spectra of m/z 147 detected from sample G31, a glioblastoma with wild-type IDH1.

Using tandem MS analysis ($MS^2$) with a linear ion trap mass spectrometer the peaks at m/z 147 are further characterized. Tandem MS analysis of m/z 147 from a glioblastoma sample with wild-type IDH1 (i.e., the less intense peak noise levels) reveals main fragment ions at m/z 89 and m/z 103 (see FIG. 7). However, in an oligodendroglioma with the IDH1 R132H mutation, the main fragment ion generated from m/z 147 is m/z 129, which corresponds to a neutral loss of a water molecule from 2-HG (FIG. 3). Further characterization of m/z 129 with an additional round of tandem MS analysis (MS3) yields two additional fragment ions at m/z 101 and m/z 85, corresponding to neutral losses of CO and $CO_2$, respectively (FIG. 4). Identical $MS^2$ and $MS^3$ results are obtained when purified L-α-hydroxyglutaric acid is subjected to tandem MS experiments (FIGS. 5 and 6).

Figure 8:
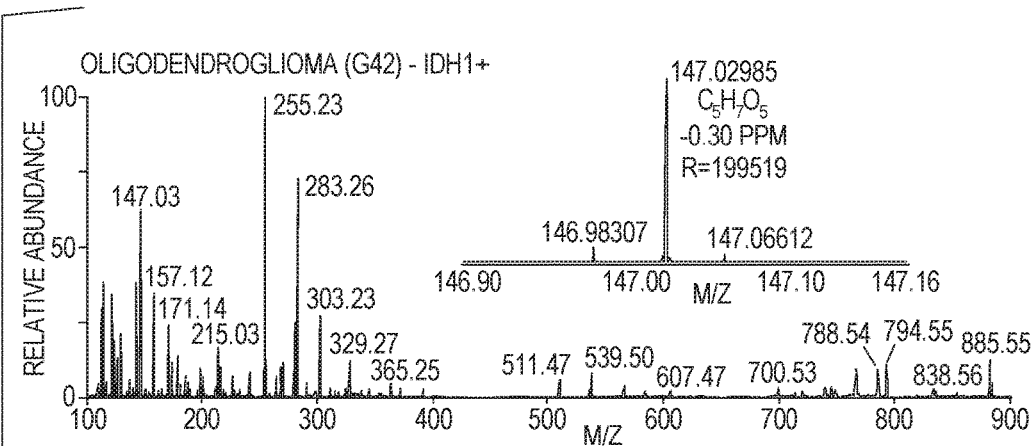
FIG. 8 shows a negative ion mode DESI-MS mass spectra obtained in a LTQ Orbitrap mass spectrometer from m/z 100 to 1000 for samples G42, an oligodendroglioma with the IDH1 R132H mutant and G29, a glioblastoma with wild-type IDH1. Insets show zoom in region m/z 146.90-147.16.
Figure 8:
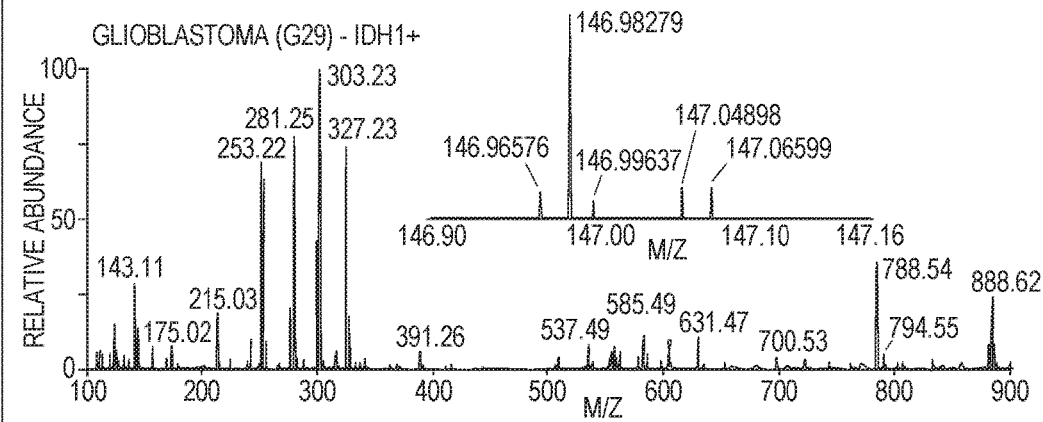

The peaks may be further characterized using a high-resolution LTQ Orbitrap mass spectrometer. DESI-MS mass spectra from an IDH1 R132H mutant sample show a prominent peak at m/z 147.02985, with a mass resolution of ~200,000 in the negative ion mode (FIG. 8). This matches the 2-HG molecular formula ($C_5H_7O_5$) with a very low mass error of 0.3 ppm. Tandem MS of the standard 2-HG at m/z 147.02982 using high resolution MS confirms the main fragment at m/z 129.01953 which corresponds to neutral loss of water ($C_5H_5O_4$, 1.7 ppm mass error), and $MS^3$ fragments m/z 101.02455 ($C_4H_5O_3$, 1.32 ppm mass error) and m/z 85.02966 ($C_4H_5O_2$, 1.88 ppm mass error) that correspond to further neutral losses of CO and $CO_2$ from m/z 129, respectively. In all, these results confirm the ability to reliably detect 2-HG with DESI-MS.

FIGS. 11a and 11b shows an example application of the invention and includes the levels of 2-HG recognized using DESI-MS in a panel of 35 human glioma resection specimens. The samples include primary and recurrent oligodendrogliomas, oligoastrocytomas and astrocytomas of different grades, including Grade IV glioblastoma samples. The presence of the R132H mutation in IDH1 for these exemplary samples was determined by immunohistochemistry using a previously validated antibody that selective recognizes the R132H mutant epitope and not the wild-type epitope from IDH1. 2-HG levels were measured using with a linear ion trap LTQ DESI-MS rapidly, directly from frozen tissue sections, and without any sample preparation. The 2-HG signal was normalized at m/z 147 to the levels of the forty most abundant lipid species detected from the glioma samples. This allowed a determination of the relative levels of 2-HG from each sample. Levels of 2-HG in R132 mutant IDH1 tumors ranged from 5 to 35 μmol per gram of tumor. Nearly all of the tumors that lacked the R132H mutation had over 100-fold less 2-HG (see FIGS. 11a and 11b).

As a supplement to the above characterizations, two-dimensional DESI-MS analysis provides excellent spatial resolution without damaging the tissue, which can subsequently be stained with H&E dyes and visualized by standard light microscopy. Because the analyzed tissue remains intact, correlating the amount of metabolite with its originating source (e.g., stroma, blood vessel, tumor or normal non-neoplastic tissue) is now possible and practical. In addition, monitoring metabolite profiles simultaneously with lipid profiles (and their lipid-based tumor classifiers) will add to the diagnostic specificity and expand understanding of tumor cell heterogeneity at a precise molecular level.

Moreover, three-dimensional MRI mapping allows a correlation between radiologic imaging features and abundance of metabolites. Intraoperatively, in advanced multimodality image guided operating facilities, a surgeon could review visual information of the resection field and DESI-MS information about metabolite abundance and tumor classifiers all in the context of pre-operative and intra-operative radiological landmarks. Fluidly integrating all of this information, in a rapid timeframe, significantly enhances a surgeon's capacity to achieve optimal tumor resection and would provides the foundation for surgery guided by metabolite-imaging mass spectrometry.

Figure 9:
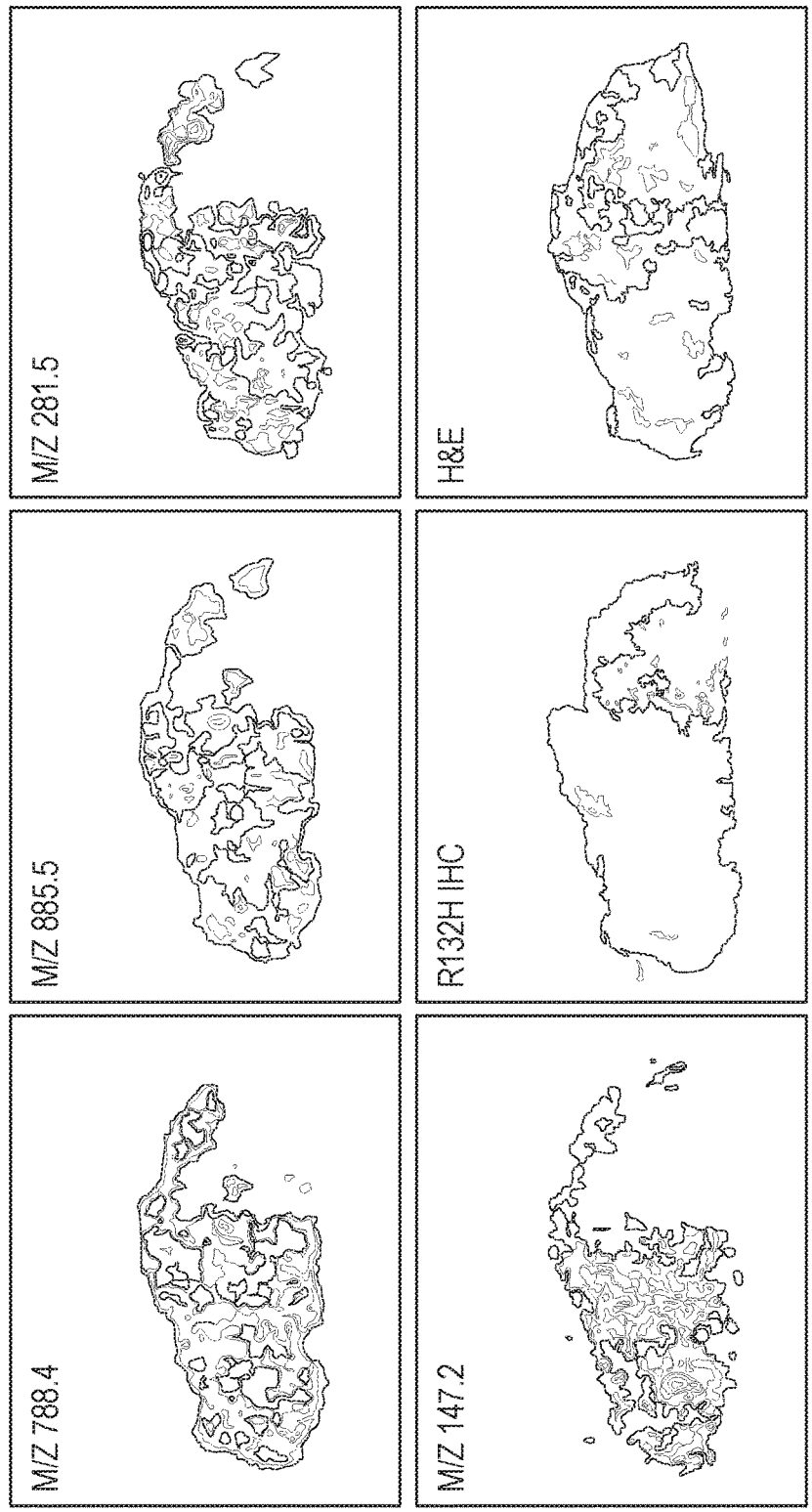
FIG. 9 shows a negative ion mode DESI-MS images from sample G30, a glioblastoma with the IDH1 R132H mutation. The panels show the distribution of ions m/z 788.4, m/z 885.5, m/z 281.5 and m/z 147.2 (identified as 2HG). Optical images of R132H IHC and H&E stained tissue sections are shown.

As an example, 2D-DESI-MS was used to evaluate the distribution of 2-HG and other diagnostic lipid species in a number of the glioma specimens discussed above with respect to FIGS. 11a and 11b. DESI-MS ion images of a densely cellular glioblastoma with wild-type IDH1, showed characteristic lipid species but m/z 147 was not detected. In contrast, in a densely cellular glioblastoma with mutant IDH1, accumulation of 2-HG (m/z 147) was observed in the region with high tumor cell concentration and was essentially absent in an abutting region containing only hemorrhage. Lipid species that are characteristic for glioblastoma (e.g., m/z 788.4, m/z 885.5 and m/z 281.5) fully overlapped with the distribution of 2-HG (FIG. 9). Similar borders between IDH1 mutant tumor cells and regions of non-neoplastic brain tissue were observed in other samples. These results provide a clear visual demonstration that DESI-MS can rapidly discriminate tumor cells with mutations in IDH1 from tissues without mutations in IDH1.

Intraoperatively, this ability could help detect glioma margins (i.e. where glioma cells interface with non-neoplastic brain tissue). Integrating the 2-HG information derived from DESI-MS with a patient's radiological imaging data would greatly empower a surgeon's intraoperative decision making FIG. 10 and FIG. 12 show an example of how to integrate these two forms of information.

Figure 10:
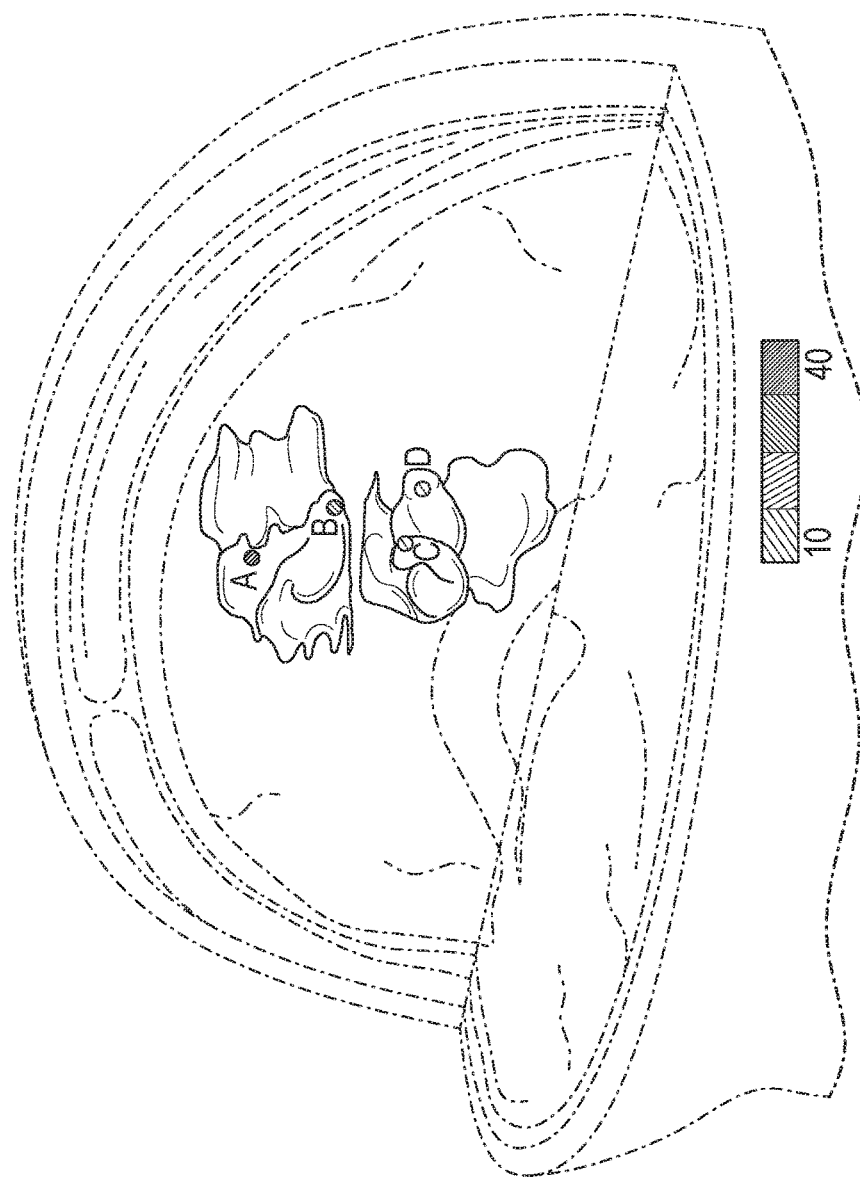
FIG. 10 is a visualization of 2-HG levels over a 3D-MRI volume reconstruction.

FIG. 10 shows a 3D mapping and registration in the Advanced Multimodality Image Guided Operating (AMIGO) Suite. This advanced surgical and interventional environment at Brigham and Women's Hospital is a part of the National Center for Image-Guided Therapy. In this example, tumor cell concentration was confirmed by a microscopic visual review of the H&E stained sections and of the IDH1 R132H immunostained sections. Strong 2-HG signals were identified in samples from the center of the tumor mass that were comprised of dense tumor. Biopsies from the margins of the radiographic mass contained low concentrations of infiltrating glioma cells as determined by H&E and IDH1 R132H stains. In those samples low to negligible levels of 2-HG were detected. As the level of 2-HG indicates the tumor cell concentration in the total tumor volume, this methodology could be very valuable for detecting tumor margins during surgical interventions.

The following is a detailed account of how one example of the invention was performed during development and conception of the present disclosure.

Tissue Samples:

The tissue samples used in this study were obtained from Brigham and Women's Hospital (BWH) Neurooncology Program Biorepository collection as previously described. They were obtained and analyzed under Institutional Review Board protocols approved at BWH. Informed written consent was obtained by neurosurgeons at BWH. The samples were sectioned for DESI-MS analysis as previously described. The tumors were classified in accordance with the WHO classification system. Resections of brain tumor lesions were performed using neuronavigation, with stereotactic mapping and spatial registering of biopsies performed as previously described. 3D-reconstruction of the tumor from MRI imaging data was achieved with 3-dimensional Slicer software package.

Histopathology and Immunohistochemistry

In addition to banked snap frozen samples, all cases had tissue samples that were formalin-fixed and paraffin embedded. Sections of FFPE tissue were stained with an anti-isocitrate dehydrogenase 1 (IDH1)-R132H antibody (clone HMab-1 from EMD Millipore) as previously described. Tissues were sectioned and immunostained as previously described. Hematoxylin and eosin (H&E) stained serial tissue sections were scanned using Mirax Micro 4SL telepathology system from Zeiss to generate digital optical images. Tumor content was evaluated by a trained neuropathologist (S.S.) through examination of H&E stained tissue sections and IDH1 R132H stained sections.

Identification and Quantification of 2-hydroxyglutarate by DESI-MS:

To determine if 2-HG could be detected directly from glioma tissue sections by DESI-MS, human glioma samples were tentatively analyzed in the negative ion mode using MeOH:$H_2O$ (1:1) and ACN:DMF (1:1) as solvent systems from m/z 100-1100. A description of the samples used in this study is shown in FIGS. 11a and 11b. The IDH1 status of the specimens was initially evaluated by IHC of a piece of FFPE tissue. For stereotactic cases, all biopsies were less than 0.4 cm and these specimens were divided in two (one portion was frozen for DESIMS studies and the other was processed for FFPE; the latter was used for IDH1-IHC). Experiments were initially performed using an LTQ linear ion trap mass spectrometer (Thermo Fisher Scientific, San Jose, Calif, USA). Negative ion mode DESI-MS mass spectra of samples G23, and G31 are shown in FIG. 10, using MeOH:$H_2O$ (1:1) as the solvent system. Tandem MS analysis was used for identification of the molecules species at m/z 147.2 using the linear ion trap mass spectrometer. Further characterization was performed by $MS^3$. The standard compound, L-α-Hydroxyglutaric acid disodium salt was purchased from Sigma-Aldrich Inc., Milwaukee, Wis. and was subjected to tandem MS experiments under the same conditions. Confirmation experiments were performed using a high-resolution LTQ Orbitrap mass spectrometer (Thermo Fisher Scientific, San Jose, Calif., USA). The Inventors analyzed thirty-five human gliomas samples including oligodendrogliomas, astrocytomas, and oligoastrocytomas of different grades and varying tumor cell concentrations using a linear ion trap LTQ mass spectrometer. Note that as tissue analysis by DESI-MS is performed without sample preparation but directly on tissue section, standard quantification of 2-HG as commonly performed with time consuming HPLC-MS protocols is not possible. One means by which relative levels of a certain molecule can be calculated is by normalizing its signal to a reference signal or set of signals obtained from the sample. In the study, the total abundance of 2-HG signal at m/z 147 was normalized to the sum of total abundance of the forty most abundant lipid species detected from the glioma samples by DESI-MS. As a small contribution of background signal at the same m/z 147 was present in DESI mass spectra, $MS^2$ was performed for all samples in order to confirm the presence of 2-HG. This was especially important in some IDH1 mutant samples with low tumor cell concentrations and therefore much lower abundances of 2-HG in DESI mass spectrum. If the $MS^2$ and $MS^3$ fragmentation pattern matched that of authentic 2-HG, the sample was determined to be IDH1 mutated. Discrepancies in the fragmentation pattern or absence of detectable levels of m/z 147 were interpreted as IDH wild-type by MS analysis. Results for DESI-MS analysis were obtained using two solvent systems. Note that while the solvent system DMF:ACN (1:1) favored relative abundances of low m/z ions when compared to MeOH:$H_2O$, similar trends in 2-HG were observed for both solvents. Interestingly, the ratio of m/z 147 to the sum of lipid species correlated with the tumor cell concentration determined for the sample by histopathological evaluation of serial tissue section, providing a direct measure of the 2-HG levels in tissue. Most samples that were negative for IDH1 mutation as determined by IHC did not present 2-HG in the DESI-MS mass spectra, even if the sample presented high tumor cell concentration, as confirmed by tandem MS analysis.

In DESI-MS analysis, a tissue section of ~12 μm in thickness is examined in a pixel by pixel fashion, with a sampling area of 200×200 μm$^2$ for each mass spectra acquired. A rough estimation of the total amount of 2-HG/pixel can be made by first estimating the mass of a 10 mm×6 mm human brain tissue section of 12 μm thickness to be ~0.5 mg. Each 200×200 μm$^2$ pixel therefore contains a mass of $3.3 \times 10^{-4}$ mg. From literature values, it can be then estimated that each pixel being sampled by DESI-MS spray in R132 mutant IDH1 tumors has between 2 and 12 pmol of 2-HG. Therefore, it is expected that the concentration of 2-HG/pixel in wild-type IDH1 tumors would not be within the detectable levels for DESI-MS analysis. To address this, the limit of detection of 2-HG was estimated by depositing different concentrations of standard 2-HG solutions onto mouse brain tissue, followed by DESI-MS analysis under the same experimental conditions that human glioma samples were analyzed. As observed, while a linear relationship between 2-HG concentration and total abundance of m/z 147 was not observed ($R^2=0.69$), a somewhat linear relationship was achieved between 2-HG concentration and total abundance of m/z 147 normalized to the sum of total abundance of the forty most abundant lipid species detected ($R^2=0.94$) from the mouse brain tissue by DESI-MS. These results indicate that the value of m/z 147 abundance normalized to the lipid signals provides an indication of the concentration of 2-HG in tissues. The limit of detection was roughly estimated to be approximately 3 μmol 2-HG/gram of tissue, which is lower than the reported levels of 2-HG in R132 mutant IDH1 tumors.

One of the challenges in the analysis was to determine IDH1 status by DESI-MS detection of 2-HG in samples with low tumor cell concentration from full mass spectral data. For these samples, low detectable values of m/z 147 could be initially assumed as an indication of IDH negative mutation. Nevertheless, $MS^2$ and $MS^3$ of m/z 147 enabled IDH+status confirmation for these samples, despite the low tumor cell concentration. DESI-MS imaging was performed for a few of the samples analyzed to evaluate the distribution of 2-HG and other diagnostic lipid species compared to tumor cell distribution in tissue The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

I claim:

1. A system for identifying a bio-marker using mass spectroscopy, the system comprising:
    a sample receptacle configured to receive a tissue sample;
    a mass spectrometry apparatus configured to receive the tissue sample and analyze the tissue sample using a mass spectrometry process to generate mass spectrometry data; and
    a computer system including a computer processor having access to a non-transitory, computer-readable storage medium having stored thereon instructions that cause the computer processor to:
        receive the mass spectrometry data from the mass spectrometry apparatus;
        analyze the mass spectrometry data to determine a relative abundance of a mass-to-charge ratio of about 147 m/z and a relative abundance of a mass-to-charge ratio of about 129 m/z, thereby indicating a presence of 2-Hydroxyglutarate (2-HG) in the tissue sample; and
        generate a report indicating a likelihood of cancer in the tissue sample based on the presence of 2-HG in the tissue sample.

2. The system of claim 1, wherein the computer system further includes instructions that cause the computer processor to analyze the mass spectrometry data to further characterize 129 m/z and determine the relative abundance of 101 m/z and 85 m/z indicating a presence of 2-HG in the tissue sample.

3. The system of claim 1, wherein the computer system further includes instructions that cause the computer processor to analyze the mass spectrometry data to determine a relative abundance of 103 m/z and 89 m/z indicating a presence of a wild-type isocitrate dehydrogenase 1 (IDH1) in the tissue sample.

4. The system of claim 1, further comprising a report generator configured to deliver the report indicating the health of the tissue.

5. The system of claim 1, further comprising a database of data about bio-markers and wherein the computer system further includes instructions that cause the computer processor to access the database and compare the mass spectrometry data to the data about bio-markers to determine the presence of 2-Hydroxyglutarate (2-HG) in the tissue sample.

6. The system of claim 5, wherein the computer system further includes instructions that cause the computer processor to determine relative abundance of at least 147 m/z to determine the presence of 2-Hydroxyglutarate (2-HG) in the tissue sample.

7. The system of claim 1, wherein the mass spectrometry apparatus includes a desorption electrospray ionization apparatus.

8. The system of claim 1, further comprising a tracking system arranged to correlate a spatial location the tissue sample was removed from with the mass spectrometry data.

9. The system of claim 8, further comprising a report generator configured to display the spatial location and a report indicating the likelihood of the presence of 2-HG each spatial location in the tissue sample.

10. A method of identifying cancerous cells, the method comprising:
    collecting a tissue sample;
    analyzing the tissue sample with a mass spectrometry system;
    determining a relative abundance of a mass-to-charge-ratio of about 147 m/z;
    determining a relative abundance of a mass-to-charge ratio of about 129 m/z; and
    based at least in part on the determined relative abundance of 147 m/z, generating a report indicating a likelihood that the tissue sample includes cancerous cells.

11. The method of claim 10, further comprising characterizing the 129 m/z to determine a relative abundance of a mass-to-charge-ratio of about 101 m/z and 85 m/z.

12. The method of claim 10, further comprising determining a relative abundance of a mass-to-charge-ratio of about 103 m/z and 89 m/z.

13. The method of claim 10, further comprising:
    determining a relative abundance of a mass-to-charge-ratio of about 129 m/z;
    characterizing the 129 m/z to determine a relative abundance of a mass-to-charge-ratio of about 101 m/z and 85 m/z;
    determining a relative abundance of a mass-to-charge-ratio of about 103 m/z and 89 m/z; and
    based at least in part on the determined relative abundance of 129 m/z, 103 m/z, 101 m/z, 89 m/z, and 85 m/z, determining whether the tissue sample includes cancerous cells.

14. The method of claim 13, further comprising indicating a presence of 2-Hydroxyglutarate (2-HG) in the tissue sample if the relative abundances of 129 m/z, 101 m/z, and 85 m/z are equal to or greater than predetermined levels.

15. The method of claim 13, further comprising indicating a presence of a wild-type isocitrate dehydrogenase 1 (IDH1) in the tissue sample if the relative abundances of 103 m/z and 89 m/z are equal to or greater than predetermined levels.

16. A system for use in an operating room, the arrangement comprising:
    a sampling probe configured to collect a tissue sample;
    a mass spectrometry apparatus in communication with the sampling probe and configured to receive the tissue sample and analyze the tissue sample using a mass spectrometry process to generate mass spectrometry data;
    a computer system including a computer processor having access to a non-transitory, computer-readable storage medium having stored thereon instructions that cause the computer processor to:
        receive the mass spectrometry data from the mass spectrometry apparatus;
        analyze the mass spectrometry data to determine a relative abundance of 147 m/z indicating a presence of 2-Hydroxyglutarate (2-HG) in the tissue sample;
        access a database of at least one of bio-marker information and bio-marker analysis algorithms; and
        analyze the relative abundance of 147 m/z using the at least one of the bio-marker information and bio-marker analysis algorithms to determine a presence of 2-HG in the tissue sample; and
    a report generator configured to deliver a report indicating the likelihood of cancer in the tissue sample.

17. The system of claim 16, wherein the computer system further includes instructions that cause the computer processor to: determine a relative abundance of a mass-to-charge-ratio of about 129 m/z; characterize the 129 m/z to determine a relative abundance of a mass-to-charge-ratio of about 101 m/z and 85 m/z; determine a relative abundance of a mass-to-charge-ratio of about 103 m/z and 89 m/z; and indicate a presence of 2-Hydroxyglutarate (2-HG) in the tissue sample if the relative abundances of 129 m/z, 101 m/z, and 85 m/z are equal to or greater than predetermined levels.

18. The system of claim 16, wherein the computer system further includes instructions that cause the computer processor to: determine a relative abundance of a mass-to-charge-ratio of about 129 m/z; characterize the 129 m/z to determine a relative abundance of a mass-to-charge-ratio of about 101 m/z and 85 m/z; determine a relative abundance of a mass-to-charge-ratio of about 103 m/z and 89 m/z; and indicate a presence of a wild-type isocitrate dehydrogenase 1 (IDH1) in the tissue sample if the relative abundances of 103 m/z and 89 m/z are equal to or greater than predetermined levels.

* * * * *